United States Patent [19]
Vora et al.

[11] Patent Number: 5,053,343
[45] Date of Patent: Oct. 1, 1991

[54] SELECTIVE IONIZATION OF GAS CONSTITUENTS USING ELECTROLYTIC REACTIONS

[75] Inventors: Kishore N. Vora, Annandale, Va.; Donald N. Campbell, Timonium, Md.; Robert C. Davis, Jr., Westminster, Md.; Glenn E. Spangler, Lutherville, Md.; Julio A. Reategui, Cockeysville, Md.

[73] Assignee: Environmental Technologies Group, Inc., Towson, Md.

[21] Appl. No.: 319,549

[22] Filed: Mar. 6, 1989

Related U.S. Application Data

[62] Division of Ser. No. 701,898, Feb. 15, 1985, Pat. No. 4,839,143.

[51] Int. Cl.$^5$ .................. G01N 27/64; G01N 27/66; G01N 27/70
[52] U.S. Cl. .................. 436/153; 436/106; 436/116; 436/103; 436/154; 436/173; 250/424; 250/287; 324/468
[58] Field of Search ............... 436/106, 116, 103, 173, 436/154, 153; 250/424; 324/468; 422/98

[56] References Cited

U.S. PATENT DOCUMENTS

| H. 414 | 1/1988 | Young et al. | 250/423 |
| 4,203,726 | 5/1980 | Patterson | 23/232 E |
| 4,311,669 | 1/1982 | Spangler | 422/98 |
| 4,524,047 | 6/1985 | Patterson | 422/98 |
| 4,662,305 | 11/1986 | Patterson | 436/103 |

Primary Examiner—David L. Lacey
Assistant Examiner—David Redding
Attorney, Agent, or Firm—Leonard Bloom

[57] ABSTRACT

An ion mobility spectrometer, ionization detector and mass spectrometer is described having a reaction region, and a region for introducing a sample gas, liquid or solid samples into the reaction region and an electrolyte in the reaction region of an alkali salt heated to a predetermined temperature, such as room temperature to 1000° C., to provide a chemical reaction between the alkali atoms, cations or complement anions with the sample to provide product ions. The invention provides a non-radioactive ionization source for ionization of a broad class of compounds.

19 Claims, 10 Drawing Sheets

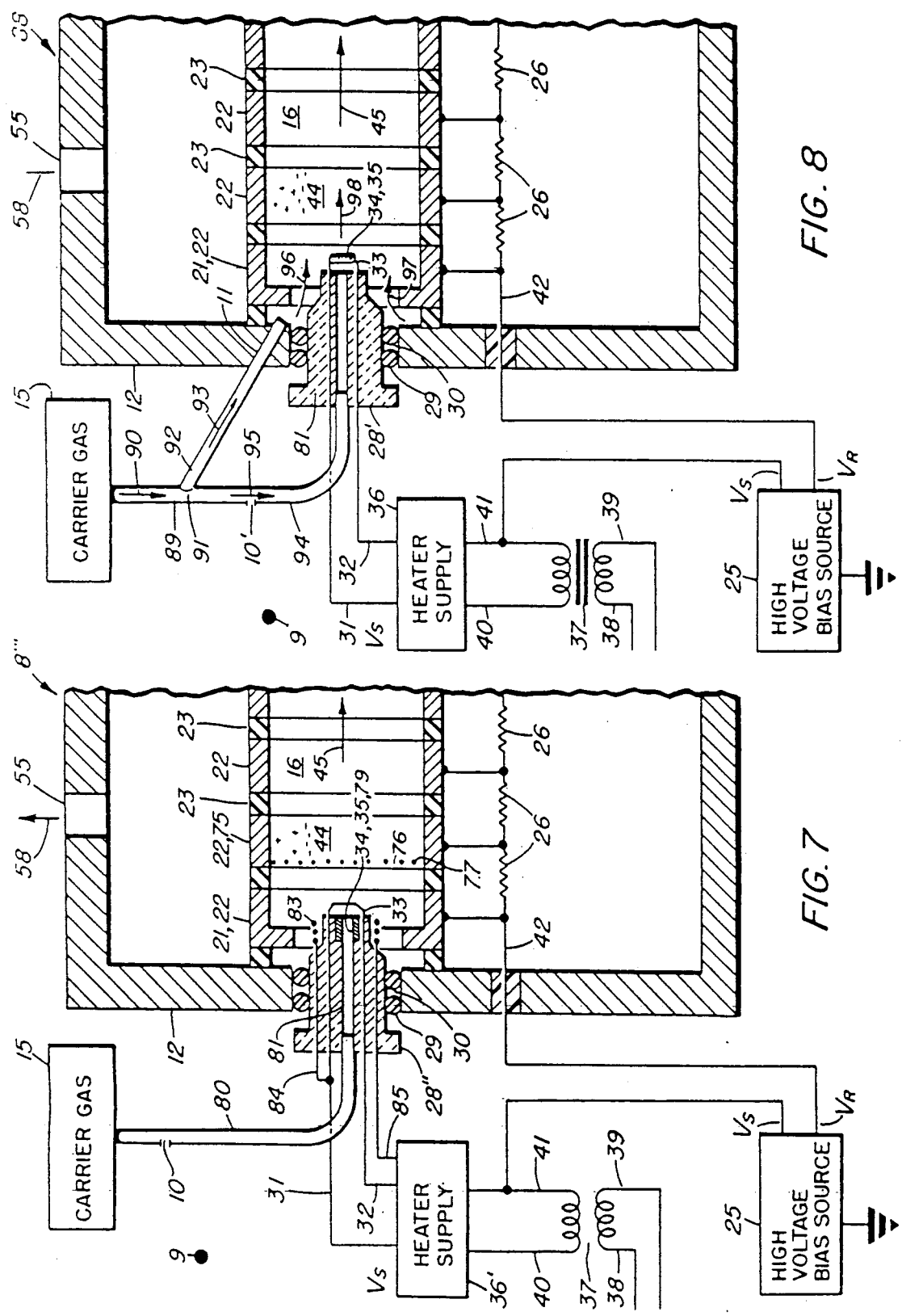

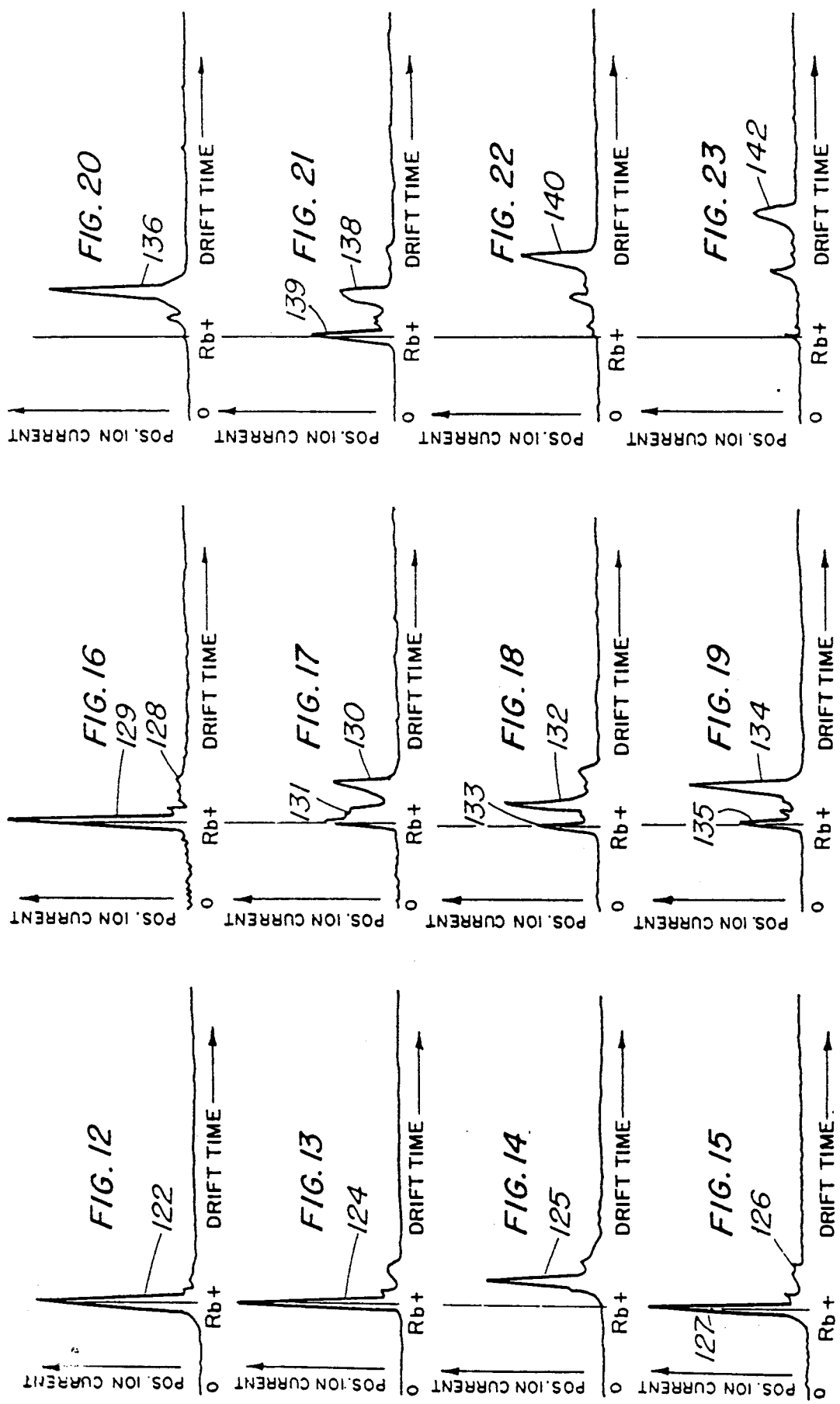

SELECTIVE IONIZATION OF GAS CONSTITUENTS USING ELECTROLYTIC REACTIONS

This application is a division of application Ser. No. 701,898, filed Feb. 15, 1985 now U.S. Pat. No. 4,839,143.

BACKGROUND OF THE INVENTION

1. Field of the Invention

This invention relates to a selective ionization source to be used with, for example, an ion mobility spectrometry, an ionization detector and a mass spectrometry and more particularly to an electrolytic ionization source using inorganic/organic salts which react with sample molecules to form product ions.

2. Description of the Prior Art

The technique of ion mobility spectrometry (IMS) was conceived in the early 1970's in order to analyze and detect organic vapors. A typical ion mobility spectrometer (IMS) detector cell consists of a reaction region for generating ions and a drift region for separation of ions. In the reaction region, reactant ions are formed using radioactive materials such as, for example, tritium, $Ni^{63}$, $Am^{241}$, etc. High energy radiation from these radioactive materials ionize a carrier gas which flows through the reaction region to form reactant ions. Coronas from a multipoint or wire array, electrons produced by photoemission and multiphotoionization have also been proposed or used as methods to produce ions in IMS. The ions formed through these processes are of both polarities and the imposed electric field determines the polarity of the ions analyzed. In the absence of an electric field imposed on the reaction region, the recombination of the positive and negative ions predominates and ion concentrations are reduced to essentially zero. In the presence of an electric field, ion concentrations are non-zero as the electric field successfully competes to extract the ions from the reaction region. The nature of the reactant ions depends on the composition of the carrier gas. The composition of the carrier gas is selected to generate reactant ions with sufficient gas phase reactivity to allow a variety of reactions to occur between the reactant ions and sample molecules which may be introduced into the carrier gas for detection. The types of reactions which are available for this purpose are shown by equations 1-3 for positive ions:

Proton transfer $$RH^+ + M \rightarrow R + MH^+ \tag{1}$$

Charge Transfer $$R^+ + M \rightarrow R + M^+ \tag{2}$$

Nucleophilic attachment $$R^+ + M \rightarrow MR^+ \tag{3}$$

Equations 4-8 show the type of reactions for negative ions:

Resonance capture $$e^-(\sim 0.5\,ev) + M \rightarrow M^- \tag{4}$$

Dissociative capture $$e^-(\sim 0.5\,ev) + M \rightarrow (M-A)^- + A^- \tag{5}$$

Charge Transfer $$R^- + M \rightarrow R + M^- \tag{6}$$

Proton abstraction $$R^- + M \rightarrow RH + (M-H)^- \tag{7}$$

Electrophilic attachment $$R^- + M \rightarrow RM^- \tag{8}$$

In equations 1-8, R is the reactant moiety and M is the neutral sample moiety. After the ion/molecule reactions, a mixture of reactant ions and product ions exists in the reaction region.

A shutter grid positioned between the reaction region and the drift region permits momentary introduction of the ion mixture generated in the reaction region into the drift region. This is accomplished by momentarily removing a blocking voltage normally applied to the shutter grid. Once in the drift region, the ion mixture drifts under the influence of an electric field to an ion collector, Faraday plate, in a time characteristic for each ion as measured from the shutter grid. The drift times for the ions and the peak amplitudes in ion current arriving at the collector provide a basis for the identification of the chemical species originally introduced into the reaction region.

The IMS technique as described above has quite a few limitations. Some of the limitations are:

1. The variety of ion/molecule reactions available for ionization using radioactive sources does not provide specificity in the presence of interferences for detection, 2. Attempts to increase specificity by using non-radioactive sources, for example multiphotoionization and photoemission, results in reduced sensitivity for detection, 3. Corona discharge sources have proven to be an unreliable source of ions due to electrode sputtering processes, 4. Complex algorithms are needed to establish identification of samples with any present technique for providing a source of ions, 5. Sample introduction may require the use of a semipermeable membrane to eliminate effects of ambient air which is described in U.S. Pat. No. 4,311,669 which issued on Jan. 19, 1982 and is assigned to the assignee herein.

6. Use and handling of the radioactive materials must comply with U.S. Government regulations.

These limitations coupled with sensor design trade-offs, for example, sensitivity, selectivity, response time, service life, size, weight, power, etc. generally result in a compromised detection system for engineered applications.

In a publication entitled "Selective Responses Of A Flameless Thermionic Detector" by Paul L. Patterson appearing in Journal of Chromatography, 167 (1978) 381-397, a flameless thermionic detector is described which uses an electrically heated bead consisting of an alkali metal compound embedded in a ceramic matrix. FIG. 6 shows chromatograms of a detector test sample at two different hydrogen flow-rates. Without any hydrogen, no response was observed from azobenzene and malathion.

In U.S. Pat. No. 4,378,499, issued on Mar. 29, 1983 to G. E. Spangler, D. N. Campbell and S. Seeb and assigned to the assignee herein, an Ion Mobility Detector is described in which selectivity and sensitivity is enhanced. As shown in FIG. 5 of '499, a reactive coating is applied to the internal wall of the reaction region. The reactive coating which may be activated by heating or by radiation from an ultraviolet source is selected to provide chemical conversion of sample molecules to a more ionizable form.

In U.S. Pat. No. 3,835,328 which issued on Sept. 10, 1974 to Harris et al. and in U.S. Pat. No. 4,075,550 which issued on Feb. 21, 1978 to Castleman et al. an ionization detector was described which utilized a radioactive source to produce beta radiation to form ions from a sample gas.

In a publication entitled "Atmospheric Pressure Ionization Mass Spectrometry" by D. I. Carroll et al. appearing in Applied Spectroscopy Reviews, 17 (3), 337–406 (1981), a general review of atmospheric ionization in mass spectrometry was provided. The use of an alkali salt was not mentioned.

Similarly, it is also desirable to provide an ion mobility spectrometer having a reaction and drift region with a doped solid electrolyte in the reaction region to react with sample molecules to form product ions.

It is further desirable to generate ions in certain equipment, for example, an ion mobility spectrometer ionization or mass spectrometer without the need for radioactive materials or without the need for hydrogen gas.

It is further desirable to provide an electrolytic ionization source which may be doped electrolyte where the electrolyte, such as alkali salts, can be adjusted to undergo general or class specific reactions with organophosphorous, nitrogen, and other organic or inorganic compounds.

SUMMARY OF THE INVENTION

An apparatus for ionizing one of more constituents in a gas is described comprising a reaction region and drift region, an electrolyte positioned in the reaction region, an inlet for introducing the gas into the reaction region, a heater for heating the electrolyte to a predetermined temperature to provide an ion reaction between the electrolyte at its surface or between electrolyte ions in the gas and selected gas constituents to form ion products in the gas.

The invention further provides a method for generating ion products in an ion mobility spectrometer, ionization detector or mass spectrometer from selected sample vapors in purified gases or ambient air comprising the steps of heating an electrolyte, such as a salt, which may, for example, be selected from the alkali/halogen salts (e.g. CsI, CsBr, KI, etc.), the alkali acid salts (e.g. $Cs_2SO_4$, $KNO_3$, $Li_3PO_4$, etc.), the ammonium salts (e.g. $NH_4NO_3$, $NH_4Cl$, etc.), the alkaline earth salts (e.g. $CaSO_4$, $BaCl_2$, etc.), salts of the transition metals (e.g. $AgNO_3$, AgI, etc.) or complex organic salts such as salts of the carboxylic and sulfonic acids, quaternary ammonium salts, etc., or other compounds (e.g. ($LaB_6$) characterized by a low work function for electron emission, and mixtures thereof to a temperature in the range from room temperature to 1000° C., dependent on the salt, passing the sample vapors in a purified or ambient air carrier gas over the electrolyte to accomplish product ion formation. Alternatively, in place of sample vapors, a liquid or solid may be deposited directly on the electrolyte for ionization. The product ions can be formed either by reactions on the surface of the electrolyte with subsequent evaporation into the gas for detection or in the gas phase above or downstream from the electrolyte involving ion/molecule reactions with reactant ions evaporated from the electrolyte. The invention further provides applying an electric field to the surface of the electrolyte to assist the movement of ions from the surface into the gas. The reactions may in some and do not in others include the introduction of hydrogen gas into the carrier gas, however, without a flame in the reaction region.

BRIEF DESCRIPTION OF THE DRAWINGS

FIG. 7 is a cross-section and schematic view of an alternate embodiment of the invention.

FIG. 8 is a cross-section and schematic view of an alternate embodiment of the invention.

FIGS. 12–23 are graphs showing the positive ion response of a solid electrolytic source in the embodiment of FIG. 1 to a variety of vapors.

DESCRIPTION OF THE PREFERRED EMBODIMENT

Figure 1:
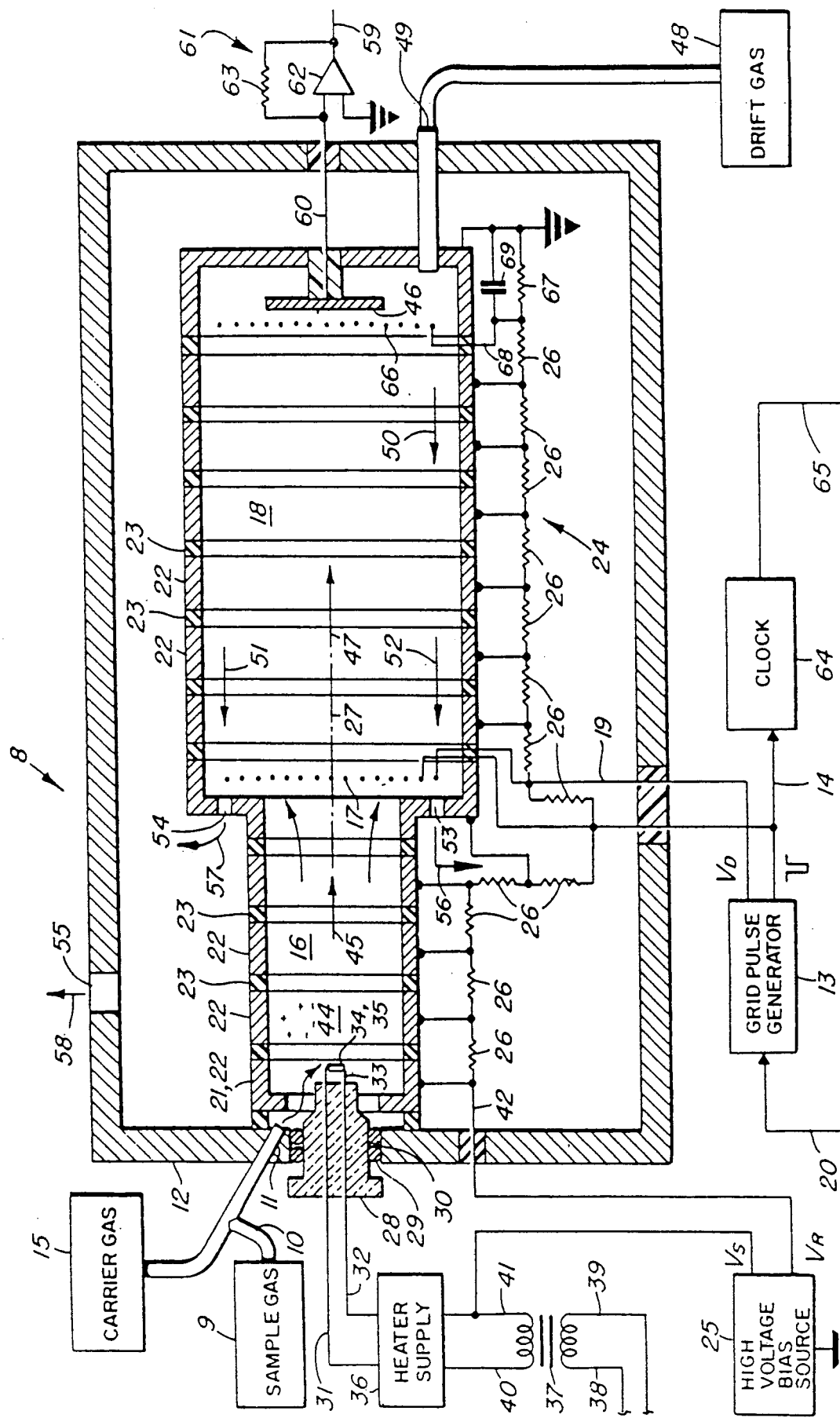
FIG. 1 is a cross-section and schematic view of one embodiment of the invention.

Referring to FIG. 1, an ion mobility spectrometer (IMS) 8 is shown for identifying one or more constituents in a sample gas 9. A carrier gas 15 with sample gas 9 passes through inlet port 11 of housing 12 into reaction region 16. The carrier gas 15 may be, for example, a high purity gas, such as nitrogen or purified air, as well as ambient air with hydrogen, for example 0.1% to 2% $H_2$, with atmospheric hydrogen or without hydrogen. The atmosphere contains about 0.01% hydrogen by volume. However, no flame is necessary in carrier gas 15, as in prior art flame detectors. Sample gas 9 may be injected into the carrier gas by means of, for example, an orifice 10 shown in FIG. 1, a syringe, a membrane inlet, an injection port, a gas chromatographic column in gas chromatography. A preconcentration device, or other suitable sample delivery means dependent on the application may also be used.

Reaction region 16 and drift region 18 is surrounded by a plurality of conductive rings 22 spaced apart from one another and secured into two cylindrical bodies, respectively, by a plurality of insulating rings 23. Alternatively, reaction region 16 and drift region 18 may be surrounded by two ceramic cylinders, respectively, internally coated with a thick film resistor as described in U.S. Pat. No. 4,390,784, which issued on June 28, 1983 to D. R. Browning et al. and incorporated herein by reference. Reaction region 16 may be heated in the range from 23° C. to 250° by resistance wires wrapped around housing 12. A high voltage bias source 25 is connected across a voltage divider 24 comprising a plurality of resistors 26 coupled in series to progressively apply increasing voltages to the conductive rings 22 or across the resistance coated ceramic cylinders to create a voltage gradient in the reaction 16 and drift 18 regions.

A shutter grid 17 divides the reaction region 16 from the drift region 18 and functions to prevent ions from entering the drift region until a pulse is received from a grid pulse generator 13 over lead 14. The shutter grid 17 may consist of a planar array of parallel wires with every other wire in electrical contact with each other and to lead 14. Alternatively, the shutter grid may be a parallel plane shutter grid consisting of two grids displaced from each other along the axis 27 of the IMS cell 8. The other wires are coupled together and to lead 19. When the grid pulse generator 13 provides a first voltage to lead 14, ions generated in reaction region 16 are collected by the grid wires 17 and are not allowed to enter drift region 18. When the grid pulse generator 13 momentarily provides a second voltage to lead 14, ions generated in reaction region 16 are allowed to enter drift region 18 without being collected by grid wires 17. The grid pulse generator 13 is referenced to the voltage divider circuit 24 by means of lead 19 and is isolated from low voltage control circuitry, for example, by optoisolators. Grid pulse generator 13 may be free running or may receive a control signal over lead 20.

Inserted into the first conductive ring 21 of reaction region 16 is an insulator plug 28 with an outside diameter less than the inside diameter of conductive ring 21. Insulator plug 28 is constructed of a material with high temperature compatibility, for example, boron nitride, ceramic, alumina, glass or MACOR. MACOR is a machinable ceramic, such as described on a 1974 Technical Data Sheet AX-3000 from Duramic Products, Inc. of Pallisades Park, N.J. The space between insulator plug 28 and conductive ring 21 allows carrier gas 15 with sample gas 9 to flow into reaction region 16. Insulator plug 28 is held in position by two O-rings 29 and 30.

Through insulator plug 28 are two spaced apart 0.127 cm (0.050 inch) terminal leads 31 and 32 to which is attached a 0.0254 cm (0.010 inch) 90% Tungston/10% Iridium, or other suitable metal, heater filament 33. Heater filament 33 is coated with an electrolyte 34. The surface 35 of the electrolyte 34 is heated by heater filament 33, which is coupled to heater supply 36 over leads 31 and 32. Heater filament 33 and electrolyte 34 is positioned in reaction region 16 to permit direct impingement of sample gas molecules 9 thereon to assure surface ionization of sample gas molecules 9 at surface 35. Heater supply 36 is isolated from ground potential through transformer 37. Transformer 37 has a first winding coupled over leads 38 and 39 to a source of power and a second winding coupled over leads 40 and 41 to heater supply 36. Lead 41 is also coupled to high voltage bias source 25 to allow the electrolytic source 34 to float at voltage $V_R$, the voltage applied over lead 42 to conductive ring 21, or above $V_R$ by a voltage $V_s$ in the range from 0 to 3000 volts. Electrolytic source 34 will have the most negative or positive voltage of the IMS cell, depending on the polarity selected for the high voltage bias source 25.

The surface temperature of electrolytic source 34 is heated without a flame or combustion to a predetermined temperature in the range from room temperature to 1000° C., depending on the electrolyte and the electric field applied to surface 35 of electrolytic source 34. The electrolytic source 34 functions to react with sample molecules 9 at or in contact with surface 35 to produce positive or negative product ions 44. Or, electrolytic source 34 functions to evaporate from surface 35 into the gas phase in reaction region 16 to react with sample molecules 9 to produce positive or negative product ions 44. Product ions 44, dependent upon the polarity of $V_R$, travel in the direction of the arrow 45 but are prevented from entering drift region 18 by shutter grid 17.

Periodically, shutter grid 17 is momentarily biased by a voltage pulse on lead 14 to allow conduction of product ions 44 into the drift region 18. Within drift region 18, product ions 44 move or accelerate towards collector 46 as shown by arrow 47. A stream of non-reactant drift gas 48 is injected into port 49 and passes through drift region 18, as shown by arrows 50–52. Drift gas 48 is exhausted through ports 53–55, as shown by arrows 56–58. Product ions 44 of different molecules attain different terminal velocities, inversely related to their collision cross section (mass), so that the presence of molecules of a constituent gas in a particular sample can be determined by sampling the detector output on lead 59 at predetermined times delayed from the initial gating pulse applied to shutter grid 17. When the product ions 44 reach collector 46, positive or negative charge is collected by collector 46 and carried over lead 60 to an input of electrometer detector 61 which amplifies and measures the current received by collector 46. Collector 46 as described here is also a Faraday plate. Detector 61 may, for example, include an operational amplifier 62 having a resistor 63 coupled between its input on lead 60 and its output on lead 59. A second input to amplifier 62 may be coupled to ground.

The output of grid pulse generator 13 is coupled over lead 14 to an input of clock 64 which measures the time elapsed since the last trigger pulse and provides a proportional signal on lead 65. When this lapse time on lead 65 is correlated with the appearance of maxima in ion current as sensed by the electrometer detector 61, the time for various ions to drift through drift region 18 can be measured. Alternatively, the ion mobility spectrum (display including all peaks) can be taken with an oscilloscope or similar equipment. The inverse of the lapse time is a measure of the mobility of the ions.

Aperture grid 66 is biased above ground by resistor 67. Resistor 67 is coupled between ground and lead 68. Capacitor 69 is also coupled between ground and lead 68. Aperture grid 66 shields collector 46 from effects of induced charge as the product ions 44 travel the length of drift region 18 before passing through aperture grid 66 to collector 46.

Figure 2:
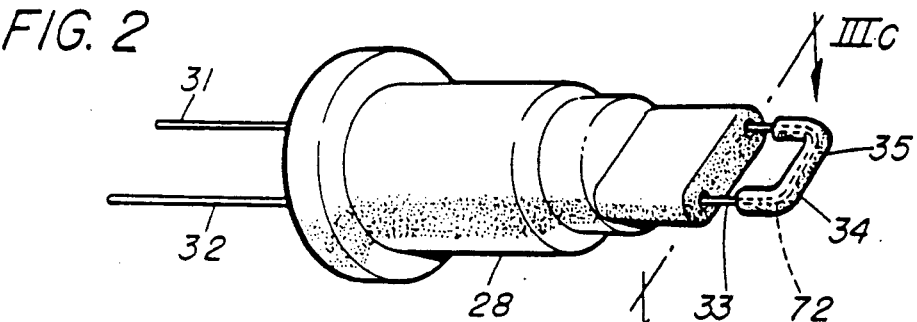
FIG. 2 is a perspective view of insulator plug 28 removed from the embodiment of FIG. 1.

FIG. 2 shows a perspective view of insulator plug 28 and electrolytic source 34 after removal from the embodiment of FIG. 1. Leads 31 and 32 pass through insulator block 28 where they are attached to heater filament 33 shown protruding from the end of insulator plug 28. As shown in FIG. 2, a thin coat of electrolyte 34 is applied to heater filament 33. When insulator plug 28 is inserted into the opening in housing 12 fitted by O-rings 29 and 30, electrolytic source 34 is positioned as shown in FIG. 1 inside conductive ring 21 and serves as a source of ions. In addition to the ability of introducing sample gas 9 through port 11, insulator plug 28 may be removed from the embodiment of FIG. 1 and heater filament 33 used to collect sample molecules either as a preconcentrator which adsorbs molecules from a gas or as a result of applying liquid solutions to heater filament 33 or electrolyte 34. In this way, salts, electrolytes, and solutions of these with sample molecules can be analyzed when insulator plug 28 is reinserted into the ion mobility spectrometer 8 shown in FIG. 1 and the heater filament 33 may be, for example heated rapidly (flashed) by heater supply 36. The direct application of sample molecules to heater filament 33 and solid electrolytic source 34, as described above, is very useful for analyzing volatile electrolytes and salts, as well as liquids.

Figure 3A:
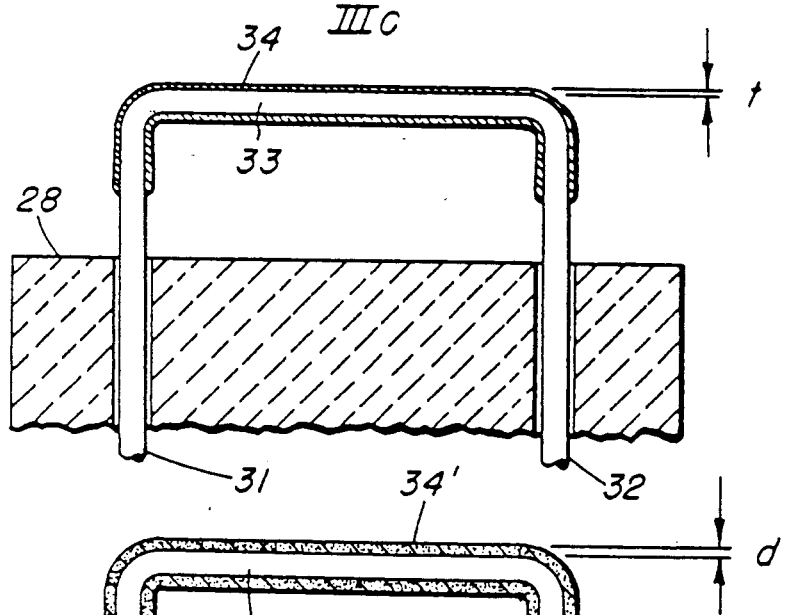
FIGS. 3A and 3B are cross-section views of alternate embodiments of a portion of FIG. 2 along the lines IIIC—IIIC of FIG. 2.
Figure 3B:
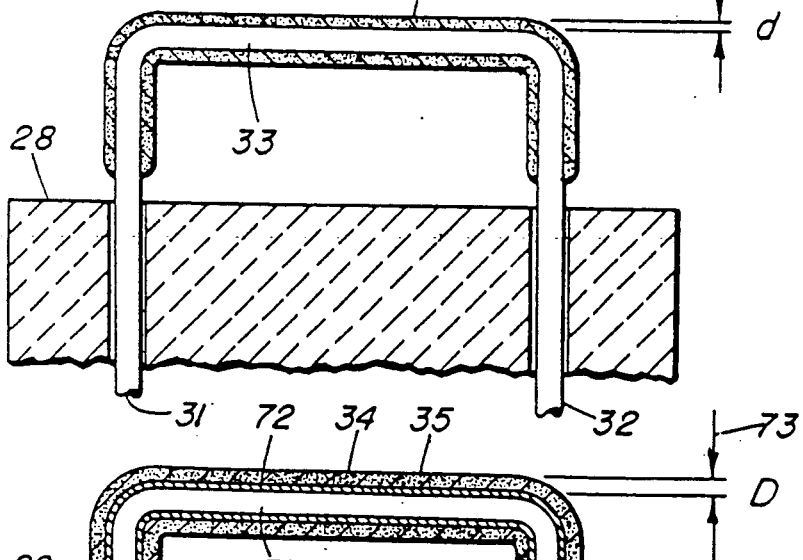
Figure 3C:
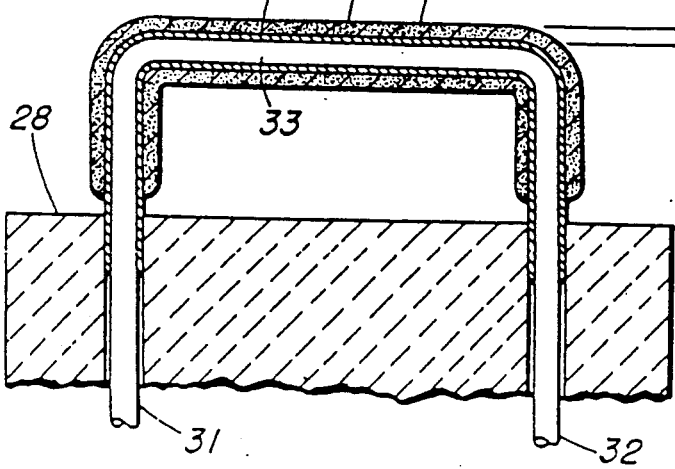
FIG. 3C is a cross-section view of a portion of FIG. 2 along the lines IIIC—IIIC of FIG. 2.

FIGS. 3A and 3B are cross-section views of alternate embodiments of a part of FIG. 2. FIG. 3C is a cross-section view of a part of FIG. 2 along the lines IIIC—IIIC. In FIGS. 3A-3C, heater filament 33 which may be a portion of leads 31 and 32 may, for example, be composed of NICHROME, platinum, iridium, rhodium or other suitable metals or materials for resistance heating. Generally, platinum (particularly 10% iridium in platinum) is more resistant to corrosion by electrolytes.

In FIG. 3A, electrolyte 34 forms a layer on heater filament 33. Electrolyte 34 may have thickness, for example, of .025 millimeters (.001 inches) shown by dimension t.

In FIG. 3B, electrolyte and cement forms a layer 34' on heater filament 33. Layer 34' may have a thickness, for example 0.64 centimeters (0.25 inches), shown by dimension d.

In FIG. 3C, heater filament 33 may be protected from corrosion by an inert layer 72, for example quartz formed from decomposition of OV-275, glass, cement without electrolyte, or cement without electrolyte containing zinc oxide. Inert layer 72 may be, for example, a thin coating on heater filament 33 in the range from 0 to 0.60 cm thick. For thicker coatings the heater filament 33 must be completely coated with the film to avoid development of hot spots in the filament which can lead to burn-out. Inert layer 72 either provides a barrier to the migration of the electrolyte 34 to heater filament 33 or inert layer 72 with zinc oxide reacts with electrolyte 34 and neutralizes it. Finally, it is advisable to provide inert layer 72 over the entire heater filament 33 to prevent neutral molecules of the electrolyte in either solid liquid or gas form from reaching heater filament 33, and corroding the heater filament 33. This provides a longer life heater filament 33.

The electrolytic source 34 is preferably a composition formed by firing an electrolyte into an alumino-silicate mixture or impregnating a glass matrix with electrolyte. The electrolytic source 34 may be coated over heater filament 33 and over inert layer 72, if provided, to form a bead or coating such that the thickness of the electrolyte is reasonably uniform around the heater filament 33, which may be preformed to assure maintenance of a uniform temperature on the surface of the coating of the electrolytic source 34.

As shown in FIG. 3C, heater filament 33, along with leads 31 and 32, may be cylindrical in shape with electrolytic source 34 forming a layer, sleeve or cylinder over heater filament 33 and inert layer 72 having a thickness D as shown by arrow 73 from surface 35 to inert layer 72.

Figure 4:
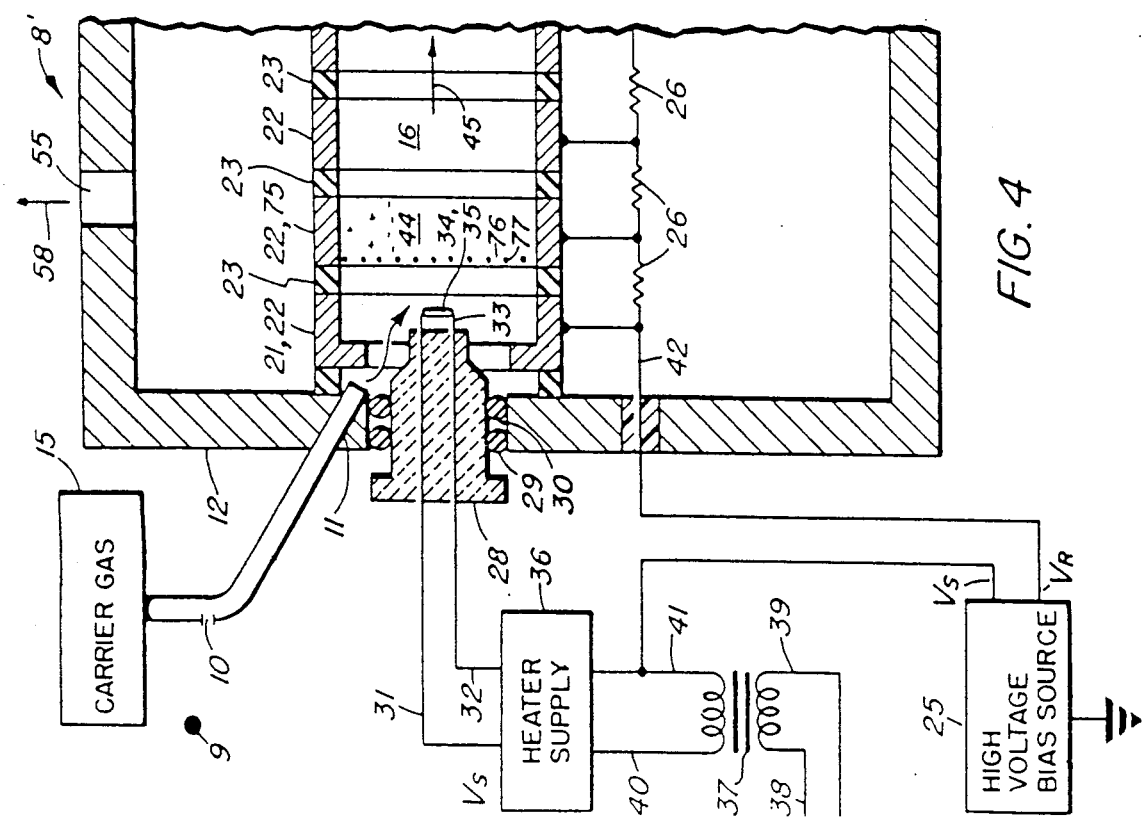
FIG. 4 is a cross-section and schematic view of an alternate embodiment of the invention.

FIG. 4 is a cross-section and schematic view of an alternate embodiment of the invention. In FIG. 4, like references are used for functions corresponding to the apparatus of FIG. 1. In FIG. 4, conductive ring 75 contains a grid 76 which extends across the end of conductive ring 75, which is also the diameter of reaction region 16. Grid 76 may be formed by conductive wires strung across one end of conductive ring 75. The wires may be positioned parallel to one another. Alternatively, the wires may cross one another forming a mesh. Grid 76 is positioned in close proximity to electrolytic source 34. Alternatively, the electrolytic source 34 may be positioned in close proximity to grid 76 having a spacing in the range from 0.01 to 1 cm. Depending upon the diameter of the electrolytic source 34 and the spacing from grid 76 depending on the potential $V_s$ supplied to electrolytic source 34, relative to the potential of grid 76, high electric field strength can be applied to the surface 35 of electrolyte 34. The electric field on surface 35 may be enhanced by $1/r$ by using a smaller diameter source 34 where r is the radius of source 34. The voltage $V_s$ of heater filament 33 may be in the range from 0 to 3000 v, for example 2000 v, with respect to the voltage of grid 76. By inserting grid 76 in reaction region 16 in close proximity of solid electrolytic source 34, the magnitude of the field strength applied to the surface 35 of electrolytic source 34 may be increased by $10^2$ to $10^4$ compared to the field strengths without grid 76. The electric field strength may be selected in a range below an electric field strength which would cause arcing between heater filament 33 and grid 76. Susceptibility to arcing will be dependent on the internal pressure selected in reaction region 16. In normal operation, the pressure internal to the ion mobility spectrometer 8 is typically 1 atmosphere.

In operation of the embodiment of FIG. 4, heater filament 33 is heated to a predetermined temperature. In addition, the voltage $V_s$ of heater filament 33, relative to grid 76, is applied to provide a strong electric field at surface 35 of the electrolytic source 34. The electric field at surface 35 facilitates ion evaporation from the electrolytic source 34. The temperature and electric field at surface 35 may be adjusted to optimize ion evaporation, while limiting neutral molecule evaporation from the electrolytic source 34. The electric field at surface 35 helps to pull ions off surface 35 into the carrier gas 15 and sample gas 9 in reaction region 16. While pulling ions off surface 35, gas phase reactions for positive ions may occur such as described by equation (3). One example of a suitable reactant ion in equation (3) is cesium or other alkali metal cations. The apparatus shown in FIG. 4 is also suitable for producing negative ions which may then be used to provide a gas phase reaction described by equations (6) and (8). In equations (6) and (8) one example of a suitable reactant ion may be iodine or other halogen anions. It is further understood in the embodiment of FIG. 4 that surface ionization may also occur when gas molecules in reaction region 16 impinge upon surface 35 in accordance with equation (9):

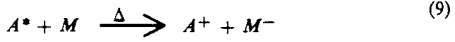 (9)

It is noted that surface ionization requires contact between the sample molecule and the thermally excited atoms on surface 35.

In the embodiment of FIG. 4 the voltage $V_D$ may be 600 v, the voltage VR may be 270 v, and the voltage $V_s$ may be 2000 v above the voltage $V_R$. The voltages $V_D$, $V_R$ and $V_s$ are of the same polarity which would be positive for positive ions and negative for negative ions. In FIG. 4 the distance between electrolytic source 34 and shutter grid 17 may be, for example, 2 cm and the distance between shutter grid 17 and collector 46 may be, for example, 4 cm. The spacing between electrolytic source 34 and grid 76 may be, for example, in the range from 0.01 to 1 cm. Grid 76 may be formed from wires having a diameter in the range from 100 micron to 0.20 cm. The spacing between parallel wires may be, for example, in the range from 100 micron to 1.5 cm.

Figure 5:
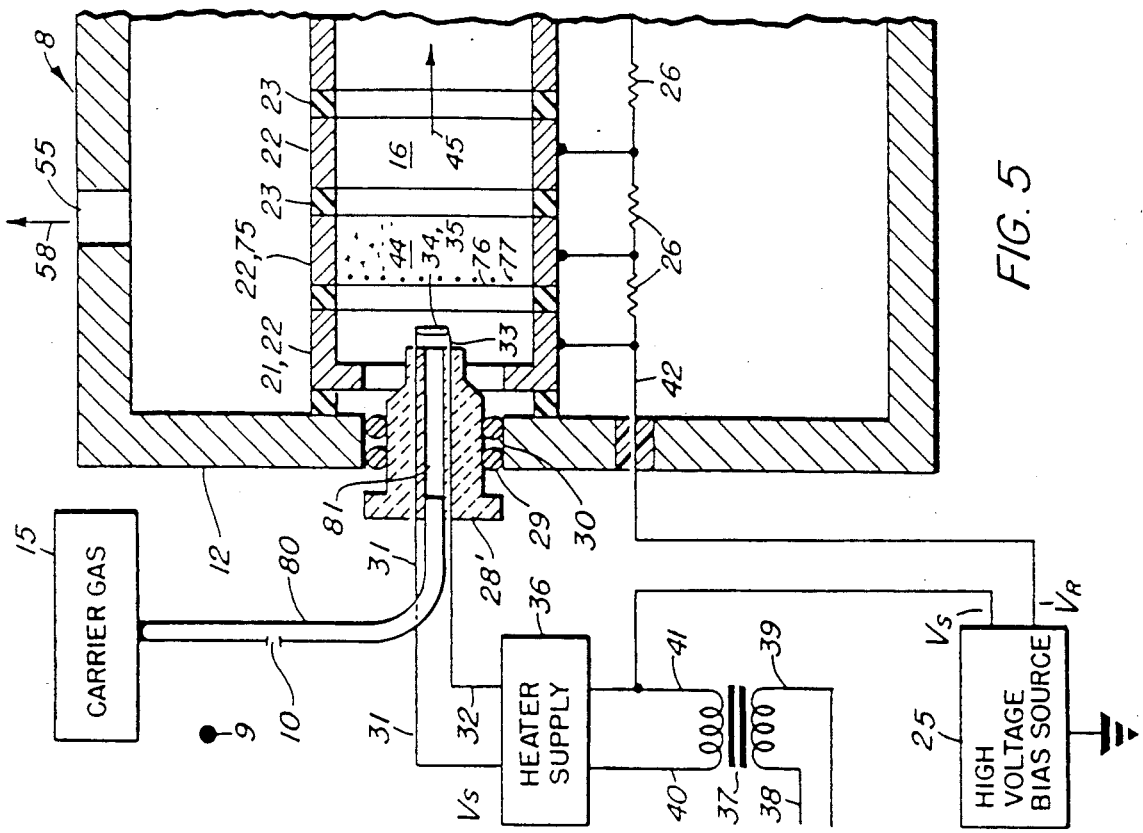
FIG. 5 is a cross-section and schematic view of an alternate embodiment of the invention.

FIG. 5 shows a cross-section and schematic view of ion mobility spectrometer 8''. In FIG. 5 like references are used for functions corresponding to the apparatus of FIG. 4. In FIG. 5 carrier gas 15 flows through tube 80 to insulator plug 28'. A passageway 81 passes through the center of insulator plug 28' to permit carrier gas 15 and sample gas 9 to impinge upon electrolytic source 34. Passageway 81 may be formed in insulator plug 28' at the time it is made or subsequently provided in insulator 28' as needed. The arrangement shown in FIG. 5 with passageway 81 through insulator plug 28' facilitates the process of surface ionization by impinging carrier gas 15 and sample gas 9 on surface 35 of electrolytic source 34.

Figure 6:
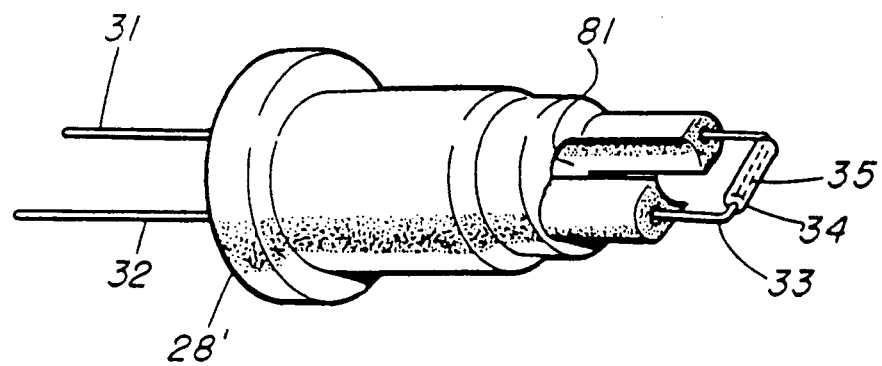
FIG. 6 is a perspective view of insulator plug 28' removed from the embodiment of FIG. 5.

FIG. 6 is a perspective view of insulator plug 28' removed from the embodiment of FIG. 5. In FIG. 6 passageway 81 is shown extending from one end to the other of insulator plug 28'. The passageway may be formed by drilling to provide clearance for a Teflon tube insert, where the material for insulator 28, is MACOR, previously referred to herein.

FIG. 7 is a cross-section and schematic view of ion mobility spectrometer 8'''. In FIG. 7 like references are used for function corresponding to the apparatus of FIG. 5. In FIG. 6 insulator plug 28' is modified to hold a reservoir 79 of electrolyte 34 interior of passageway 81, which has been enlarged at the end of insulator plug 28''. The electrolytic source 34 may, for example, be in the shape of a hollow cylinder to permit carrier gas 15 and sample gas 9 to pass therethrough and to impinge on heater filament 33. As shown in FIG. 7 a quantity of electrolytic source 34 may be deposited interior of passageway 81, which functions as a reservoir 79 by holding a large quantity of electrolyte 34 to extend the life of the electrolyte 34. The interior surface 35' of the electrolytic source 34 is in direct contact with the gases passing through passageway 81. A heater coil 83 may be positioned at the end of insulator plug 28'' to heat the electrolyte 34 to a predetermined temperature. Power to heater coil 83 may be supplied by lead 84 which is coupled to lead 31 and by lead 85 which is coupled to heater supply 36'. Heater supply 36' functions to provide power to heater coil 83 independent of the power supplied to heater filament 33.

FIG. 8 is a cross-section and schematic view of ion mobility spectrometer 88. In FIG. 8 like references are used for functions corresponding to the apparatus of FIG. 1. Carrier gas 15 flows down tube 89 as shown by arrow 90 to junction 91, wherein carrier gas 15 is divided into two streams. One stream flows through tube 92 into inlet port 11, as shown by arrow 93. The second stream flows through tube 94 into passageway 81, as shown by arrow 95. Tube 94 has an orifice or pin hole 10' for introducing sample gas 9 into carrier gas 15 flowing through tube 94. Sample gas 9 may also be introduced into tube 94 from a membrane inlet, injection port, gas chromatographic column, diffusion membrane inlet or other suitable means dependent on the application.

In operation, carrier gas 15 is divided, for example by a valve or valves, such that only 1% to 100% of carrier gas 15 in tube 89 flows through tube 94. The carrier gas 15 in tube 94 receives sample gas 9 through orifice 10' and passes through passageway 81 in insulator plug 28'. Carrier gas 15 and sample gas 9 exit passageway 81 and flow over surface 35 of solid electrolyte 34. Electrolyte 34 has been positioned in the path of carrier gas 15 and sample gas 9 at the outlet of insulator plug 28'. By reducing the carrier gas 15 flowing passed surface 35 of electrolyte 34, the reaction probability of sample gas 9 is maximized without inducing large flows of carrier gas 15 around surface 35 which tends to cool surface 35, resulting in heat losses from electrolyte 34. The remaining carrier gas 15 passes through tube 92 into reaction region 16 without flowing over surface 35. For example, carrier gas 15 in tube 92 may be introduced in reaction region 16 such that the gas mingles with the sample gas and ions down stream from the electrolytic source 34 to facilitate the purity of the normal environment of the reaction region 16, as shown by arrows 96 and 97. Arrow 98 shows the flow of carrier gas 15 and sample gas 9 passed the electrolytic source 34 prior to mixing with carrier gas 15 downstream from the position of arrows 96 and 97 which had flowed through tube 92. In FIG. 8 tubes 89, 92 and 94 may be constructed from materials including tetrafluoroethylene, stainless steel or glass. Passageway 81 may be enlarged to allow a portion of tube 94 to be inserted through passageway 81 into reaction region 16 or merely to the end of insulator plug 28'.

Figure 9:
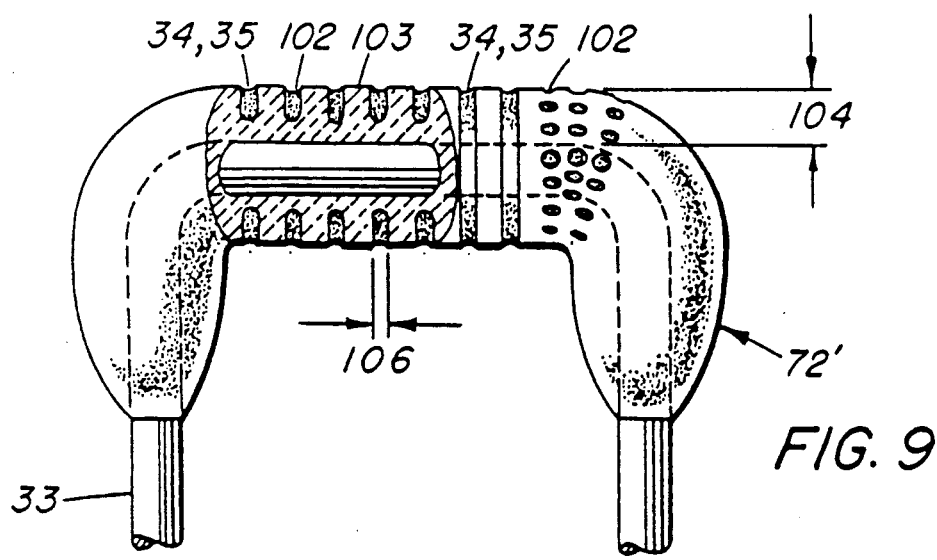
FIG. 9 is a cross-section view of an alternate embodiment of a solid electrolytic source shown in FIG. 3.

FIG. 9 is a cross-section view of an alternate embodiment of an electrolytic source 34 shown in FIG. 3. In FIG. 9 like references are used for functions corresponding to the apparatus of FIG. 3. In FIG. 9 an inert layer 72' is applied to heater filament 33, which functions to protect heater filament 33 from chemical attack and to hold solid electrolyte 34 in grooves or pores 102 in inert layer 72'. The indentations, grooves or pores 102 function to hold electrolyte 34 in excess quantities to extend the life of the electrolytic source 34. Grooves or pores 102 with solid electrolytic source 34 form a reservoir from which the rate of evaporation of electrolyte 34 may be controlled. Inert layer 72' may have a uniform thickness from the surface of heater filament 33 and the outer surface of inert layer 72', as shown by arrow 104. The outer surface 103 of inert layer 72' between grooves or pores 102 essentially reduces the surface area of electrolyte 34 compared with a completely coated surface as shown in FIGS. 3A–3C. Grooves or pores 102 may extend in inert layer 72' around heater filament 33 in the form of rings, a continuous thread or voids. Alternately, grooves or pores 102 may be microscopic indentations as might be provided by microporous ceramic and sieve materials or by foam metals. Grooves or pores 102 may have a width shown by arrow 106 in the range from 3 angstroms to 0.16 cm. Heater filament 33 may also be in the form of a coil, helix or spiral, as well as an arc or part of a polygon between leads 31 and 32.

Figure 10:
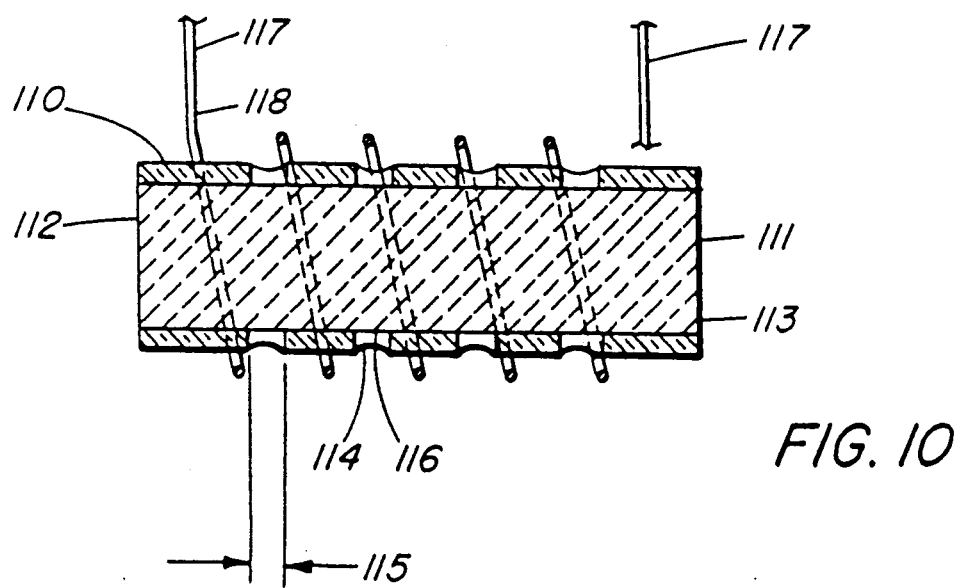
FIG. 10 is a cross-section view of an alternate embodiment of a solid electrolytic source shown in FIG. 3.

FIG. 10 is a cross-section view of an alternate embodiment of a solid electrolytic source 34. A tube 110 which may be, for example, porous and made of ceramic or other suitable material is filled with electrolyte 111. Ends 112 and 113 of tube 110 may be opened or sealed, depending upon the electrolyte. Tube 110 may have holes 114 which are spaced apart and which may have a diameter in the range from 25 to 1000 microns shown by arrow 115. Holes 114 expose a portion of the surface 116 of solid electrolyte 111 to allow its evaporation rate to be controlled. A heater filament 117 having a protective coating 118 is wrapped around tube 110 and functions to heat tube 110 and solid electrolyte 111 to a predetermined temperature. Heater filament 117 is coupled to leads 31 and 32. Protective coating 118 may be formed by heating heater filament 117 to a temperature below the flash point of a silicon grease, such as in the range from 300° to 500° C. One example of a silicon grease suitable to form a coating is dicyanoallyl silicone identified as OV-275 and listed as Item no. 08251 by Applied Science located in Deerfield, Illinois. When OV-275 is applied to heater filament 117, it decomposes and rearranges itself to leave behind a thin layer of quartz ($SiO_2$) on the surface of heater filament 117. The other decomposition products resulting from the process can be removed with a solvent such as chloroform. The solid electrolytic sources as shown in FIGS. 9 and 10 are suitable for operation in the embodiments of FIG. 1, 4, 5 and 8.

The electrolytic sources as shown in FIGS. 3A, 9 and 10 provide an improvement on a cement impregnated electrolytic source shown in FIGS. 3B and 3C, since a cement impregnated solid electrolytic source due to its bulk requires excessive power to heat the source (6 to 7 watts), its initial operation causes excessive amounts of salt to evaporate and coat the internal surfaces of insulating rings 23, of the ion mobility spectrometer causing shorts to develop within the cell, particularly at high temperature, and gives rise to peculiar flow rate dependent characteristics. Furthermore, sources based on impregnated cement provide no negative ion response in the ion mobility spectrometer, the electrolyte melts causing electricity to flow through the electrolyte rather than the heater filament, and the ion current obtained from the source goes through a maximum as the source temperature is increased. Therefore, the cement impregnated source has become less attractive as the preferred approach to the design of an electrolytic source. Impregnated ceramic, glass or alumino-silicate sources offer advantages in purity of materials which can be used to construct the source and a simple coat of electrolyte on a heater filament provides simplicity of design.

Figure 11:
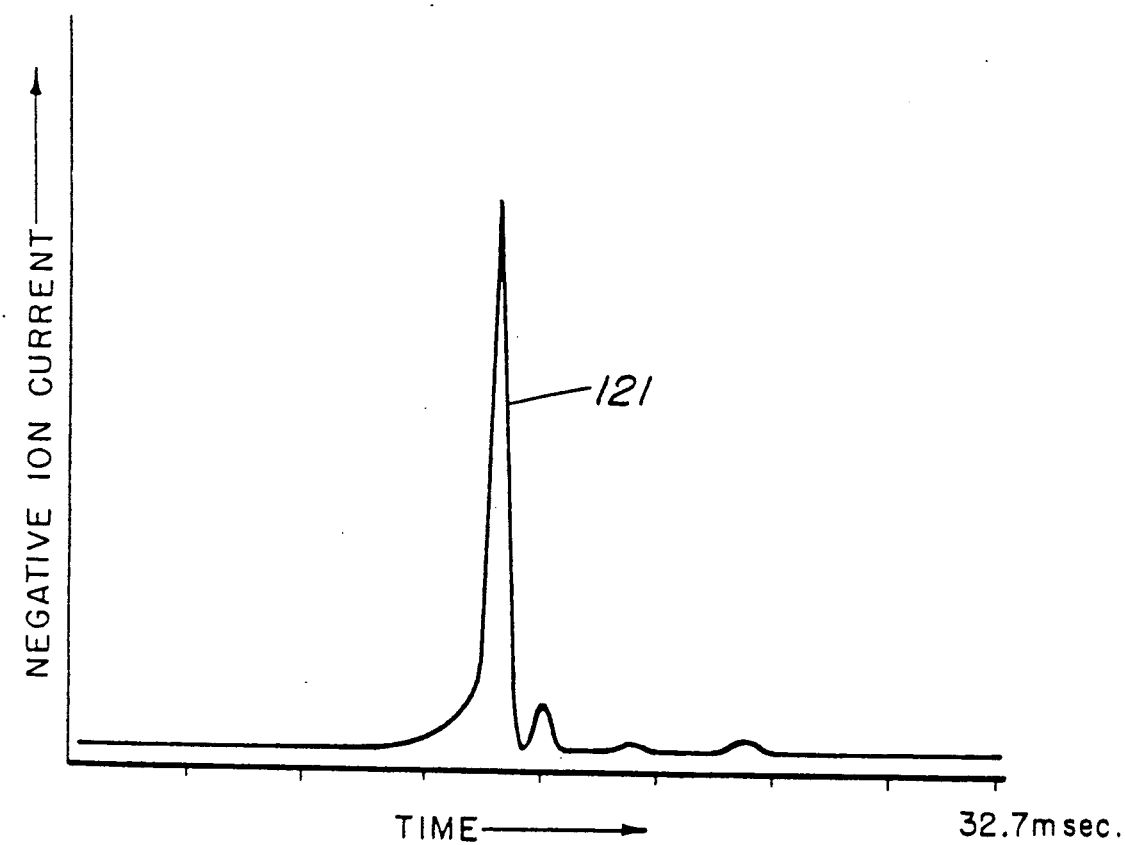
FIG. 11 is a graph showing the negative ion response of a solid electrolytic source in the embodiment of FIG. 1 of Phosdrin vapor.

FIG. 11 is a graph showing the negative ion response of the embodiment of FIG. 1. An electrolytic source 34 of Dylon-ClO cement impregnated with either cesium bromide (CsBr) or rubidium sulphate ($Rb_2SO_4$) was used with similar results. The electrolytic source 34 was baked several weeks at low power to remove impurities from the cement. Without baking, a response was observed from phosdrin but was masked by interfering impurity peaks. In FIG. 11 the ordinate represents negative ion current and the abscissa represents ion drift time. Phosdrin was introduced into a purified air carrier gas 15 containing no hydrogen and flowed past electrolytic source 34 which was heated. Curve 121 shows a negative ion current at the output of detector 61 occurring at about 12.8 ms. In FIG. 11, the response to phosdrin is believed to be due to the surface reaction shown by equation (10):

$$A^* + M \xrightarrow{\Delta} A^+ + M^- \qquad (10)$$

where $A^*$ is a thermally excited alkali metal atom, rubidium, M is the sample molecule, phosdrin, $A^+$ is the ionized alkali cation and $M^-$ is the ionized sample molecule or a fragmemt thereof. The surface reaction of equation (10) is believed to occur because of the low ionization potential of the alkali metals, such as cesium and rubidium. However, the reactions to produce negative ions may also be electrochemical, catalytic, thermionic, dissociative, etc. or any combination thereof. The response as shown in FIG. 11 gradually disappeared after several weeks of continuous operation, but could be regained by recoating the heater filament 33 with additional electrolytic source 34.

FIGS. 12-23 are graphs showing the positive ion response of an electrolytic source 34 in the embodiment of FIG. 5 without grid 76 to a variety of vapors. In FIGS. 12-23 the ordinate represents positive ion current and the abscissa represents ion drift time. An electrolytic source 34 of rubidium nitrate mixed with Sauereisen cement 29 was used as shown in FIG. 3B to obtain the graphs for FIGS. 12-23. The cement used was Sauereisen 29 cement, available from Sauereiesn Cement Co., Pittsburgh, Pa. The electrolytic source 34 was baked for several weeks to remove impurities from the cement. With rubidium nitrate as the electrolytic source 34, alkali cations, rubidium, was observed from the source as reactive ions (FIG. 12) which undergo attachment reactions with sample molecules (FIGS. 13-23). The gas phase reaction is shown in equation (11):

$$A^+ + M \rightarrow MA^+ \qquad (11)$$

In equation (11) $A^+$ is the alkali cation, rubidium, M is the sample molecule, and $MA^+$ is the attached complex.

In FIG. 12, curve 122 shows the positive ion current of reactant ions, rubidium from electrolytic source 34 in FIG. 1. Curve 122 was obtained while a carrier gas was introduced into reaction region 16, but with no sample gas 9. Curve 123 in FIG. 13 shows the response where sample gas 9 is ammonium hydroxide. Peak 124 is from the rubidium reactant cation. Unlike the strong response obtained from $NH_4OH$ using a conventional radioactive source for IMS, essentially no response is observed for ammonium hydroxide other than the alkali reactant cation. Curve 125, in FIG. 14, shows the response where sample gas 9 is acetone. A product ion is observed for acetone. Curve 126 in FIG. 15 shows the response where sample gas 9 is benzene. Peak 127 is from the rubidium reactant cation and hence no product ions are observed for benzene. Curve 128 in FIG. 16 shows the response where the sample gas 9 is xylene. Peak 129 is due to the rubidium cation and no product ions from xylene are observed. Curve 130 in FIG. 17 is a response from ion mobility spectrometer 8 where the sample gas 9 is ethanol. Peak 131 is due to the rubidium cation and the other peaks are product ions. Curve 132, in FIG. 18, is a response where the sample gas 9 is dimethylformamide. Peak 133 is due to the rubidium cation. Curve 134, in FIG. 19, is the response due to 3-Hexanone. Peak 135 is due to rubidium. Curve 136 in FIG. 20 is a response due to cyclohexanone. This is a saturated response where the rubidium cation is used up in the reaction. Curve 138 in FIG. 21 is a response due to phosdrin. Peak 139 is due to the rubidium cation. Curve 140 in FIG. 22 is a response due to the chemical DMMP. Curve 142 in FIG. 23 is a response due to the chemical DIMP. Attachment reactions as shown by equation (11) were verified by differences in mobilities of observed product ions obtained from proton attachment reactions in the presence of a radioactive source and alkali attachment reactions in the presence of the alkali cation. By using an electrolytic source, the ammonium ion was not observed as shown in FIG. 13. When using a radioactive source in an ion mobility spectrometer, ammonium hydroxide is ionized with the formation of an ammonium ion. Further, by using a cement impregnated source, no negative ions were observed from a source of alkali salt which was contrary to expectations.

Figure 24:
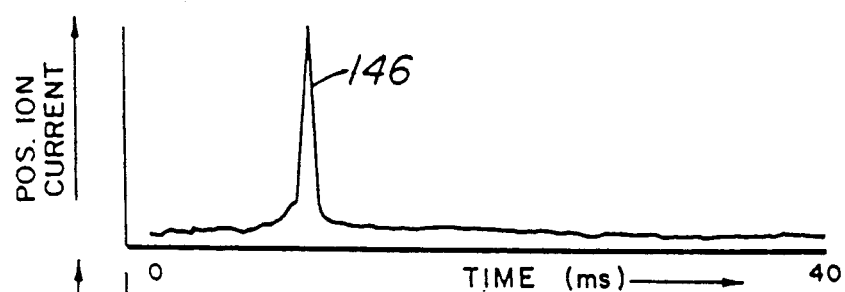
FIGS. 24–29 are graphs showing the positive ion current from a solid electrolytic source in the embodiment of FIG. 4.
Figure 25:
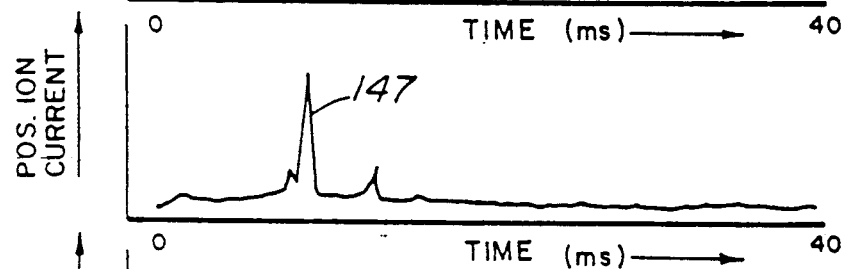
Figure 26:
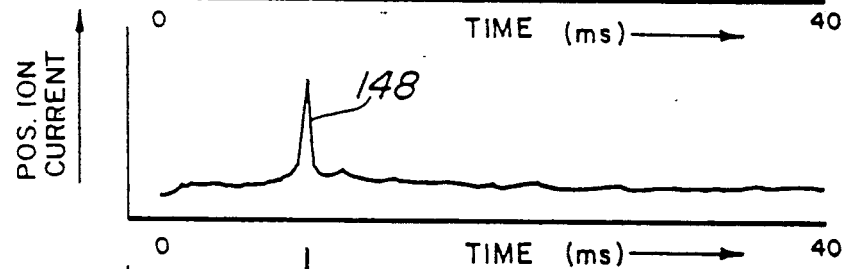
Figure 27:
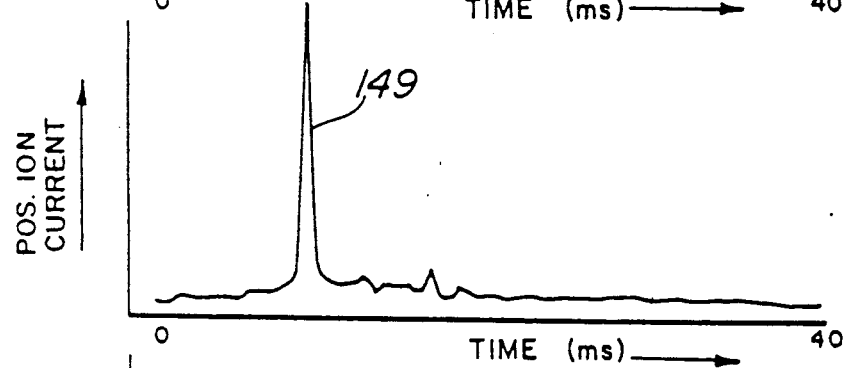
Figure 28:
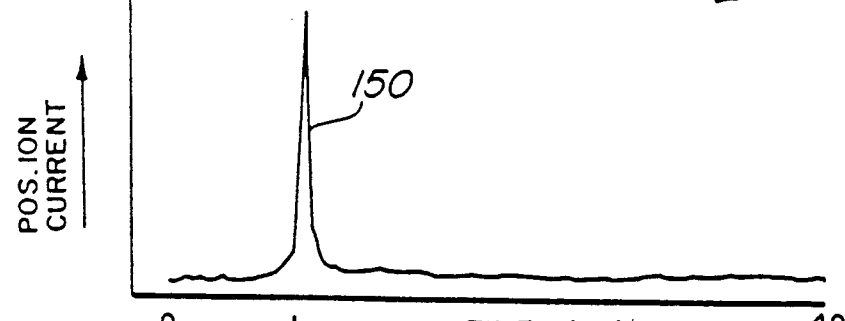
Figure 29:
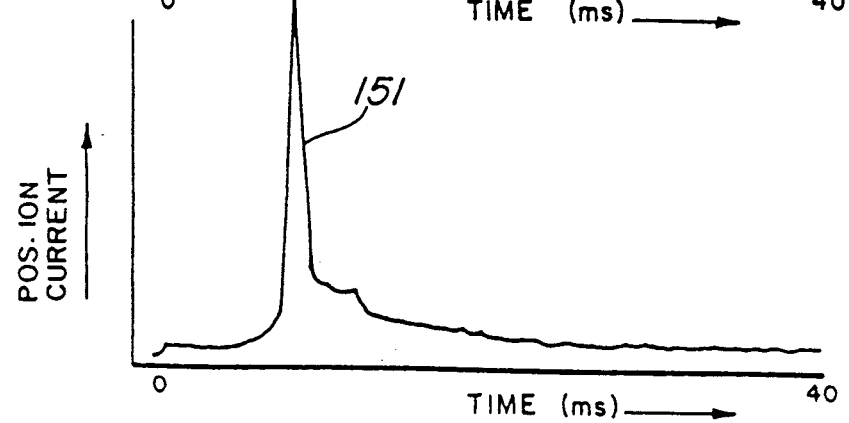

FIGS. 24-29 are graphs showing the positive ion current from an electrolytic source which is coated directly on heater filament 33 as shown in FIG. 3A in the embodiment of FIG. 5 without grid 76. In FIGS. 24-29 the ordinate represents positive ion current and the abscissa represents time. To obtain the data in FIGS. 24-29 heater filament 33 was coated with an electrolyte by depositing water solutions of electrolyte on an incandescent wire. No cement was used. The heater wire 33 along with insulator plug 28' was then inserted into reaction region 16 of ion mobility spectrometer 8" as shown in FIG. 5. In FIG. 24 curve 146 shows the positive ion current observed when lithium chloride (LiCl) was used as the electrolyte. In FIG. 25 curve 147 shows the positive ion current from potassium fluoride (KF). In FIG. 26 curve 148 shows a response from sodium chloride (NaCl). In FIG. 27 curve 149 shows a positive ion current from an electrolytic source of cesium bromide (CsBr). In FIG. 28 curve 150 shows a positive ion current from an electrolytic source of rubidium sulfate (Rb$_2$SO$_4$). In FIG. 29 curve 151 shows the positive ion current observed from an electrolytic source of ammonium nitrate (NH$_4$NO$_3$). In all cases a positive reactant ion is observed which came off the electrolytic source and could support gas phase reactions such as shown by equations (12) and (13).

$$M + R^+ \rightarrow MR^+ \tag{12}$$

$$M + R^+ \rightarrow M^+ + R \tag{13}$$

In equations (12) and (13) M is the sample molecule and R$^+$ is the reactant ion. The reactant ion would be the alkali cation in FIGS. 24-28 and the ammonium ion would be the reactant ion in FIG. 29.

Figure 30:
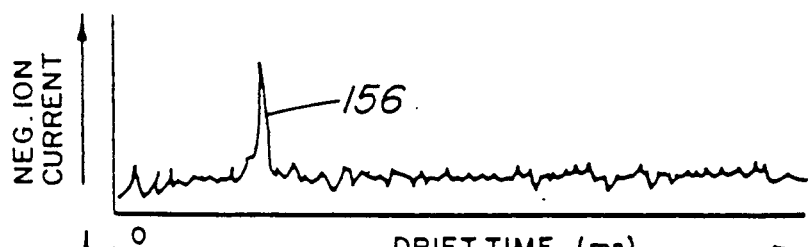
FIGS. 30–35 are graphs showing the negative ion current from a solid electrolytic source in the embodiment of FIG. 4.
Figure 31:
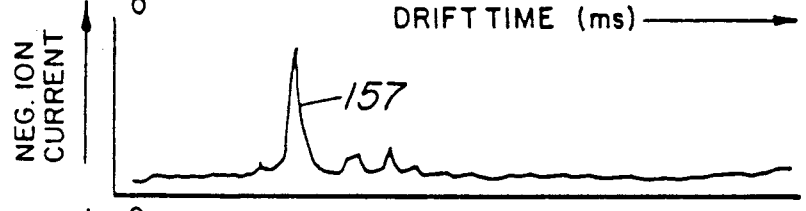
Figure 32:
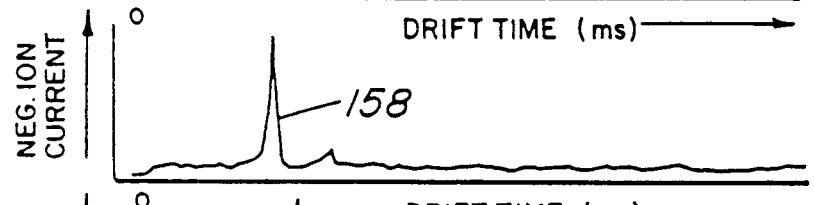
Figure 33:
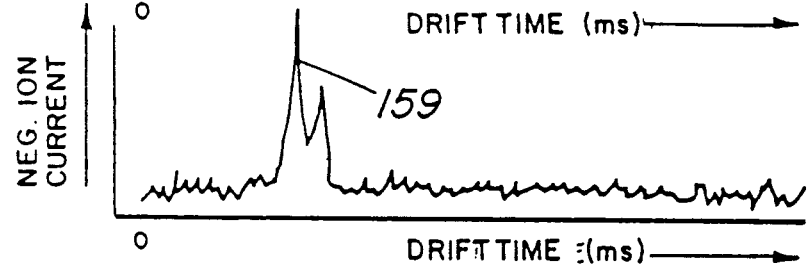
Figure 34:
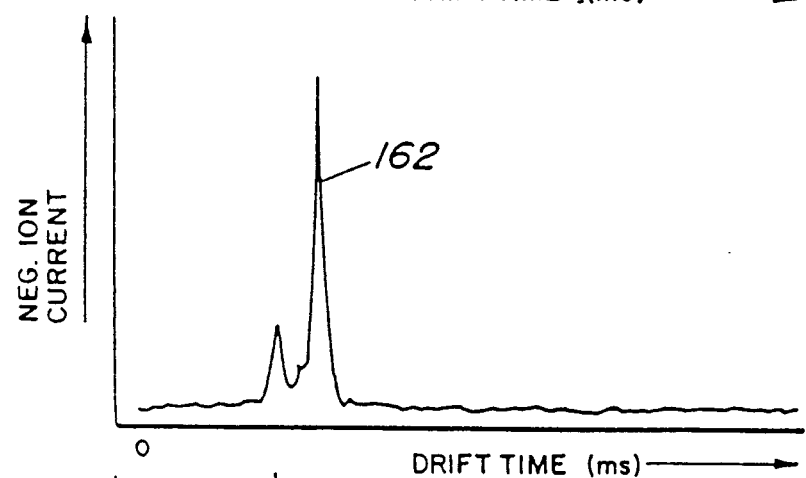
Figure 35:
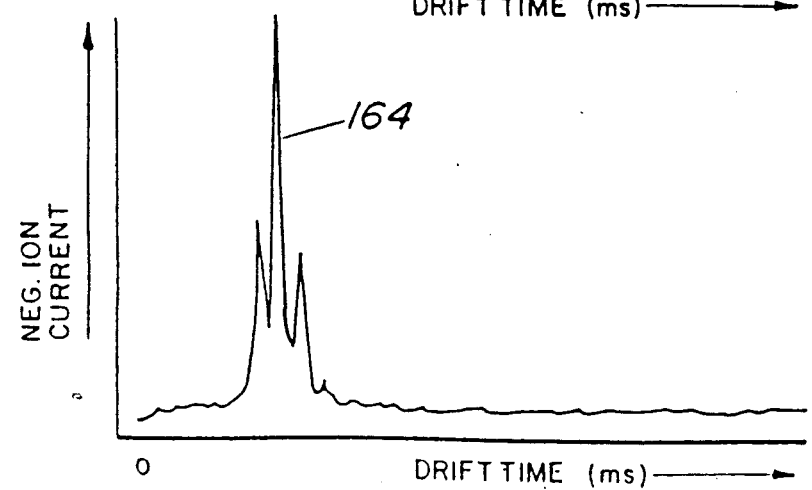

FIGS. 30-35 are graphs showing the negative ion current from a solid electrolytic source in the embodiment of FIG. 5 without grid 76. In FIGS. 30-35 the ordinate represents negative ion current and the abscissa represents ion drift time. Heater filament 33 was coated by depositing water solutions of electrolyte on an incandescent wire. After coating, the insulator plug 28 was reinserted into reaction region 16 of ion mobility spectrometer 8'. In FIG. 30, curve 156 shows the negative ion response from an electrolytic source of sodium fluoride (NaF). In FIG. 31 curve 157 shows the negative ion current from a solid electrolytic source of sodium bromide (NaBr). In FIG. 32, curve 158 shows the negative ion current from an electrolytic source of potassium iodide (KI). In FIG. 33 curve 159 shows the negative ion current from an electrolytic source of cesium sulfate (Cs$_2$SO$_4$). In FIG. 34, curve 162 shows a negative ion current from an electrolytic source of KH$_2$PO$_4$. In FIG. 35 curve 164 shows a negative ion current from an electrolytic source of K$_2$HPO$_4$. FIGS. 30-35 show that negative reactant ions are available from an electrolytic source using alkali halide salts to support gas phase reactions with a sample gas. These reactions are given by equations (14) and (15) as

$$M + R^- \rightarrow MR^- \tag{14}$$

$$M + R^- \rightarrow M^- + R \tag{15}$$

In equations (14) and (15) M is the sample molecule and R$^-$ is the reactive ion. It is noted that multiple negative ions are available from the sulfates, nitrates and phosphates which may complicate ion/molecule reaction chemistries for these salts. The reactant ions generated in each case are not all expected to be the same even though drift times are similar. Different ion/molecule reaction chemistries may be observed in each case. A consequence of this consideration is that the chemistry used for ionization can be varied and adjusted to the sample by varying the alkali source composition. In collecting the data of FIGS. 24-35, it was found that the positive or negative ion current detected depended on the temperature of heater filament 33, the electric field applied to the heater filament, and the salt used for the electrolytic source. For example, the ammonium ion from the ammonium salt could be generated at very low source heater powers when compared to other salts. Lower heater powers were also required to generate ions from CsI than from the other alkali/halide salts.

In the embodiment of FIG. 1, carrier gas 15 and drift gas 48 are shown exiting ports 53-55. An alternate arrangement for operation of ion mobility spectrometer 8 would be to introduce carrier gas 15 at ports 53 and 54 with the drift gas 48 and carrier gas 15 flowing through reaction region 16 in the opposite direction shown by arrow 45 and out through inlet port 11 to the exterior of housing 12. Another alternate embodiment would be to introduce drift gas 48 at ports 53 and 54 which would flow through drift region 18 along with carrier gas 15 and exit out port 49. Another alternate embodiment would be to seal up ports 53 and 54 and allow carrier gas 15 to flow through drift region 18 and out port 49 with drift gas 48 disconnected. The latter two alternate embodiments appear the least desirable. One reason for using the first alternate approach with the carrier gas 15 and drift gas 48 exiting port 11 is to prevent condensation of electrolyte 34 on conducting rings 22, insulating rings 23 and shutter grid 17. Condensed vapors of electrolyte on the interior walls of regions 16 and 18 tend to short-out or distort the electric field within regions 16 and 18. In addition, drift gas flowing through the reactor decreases the response time of the instrument as might be required when it is coupled to a gas chromatograph.

Figure 36:
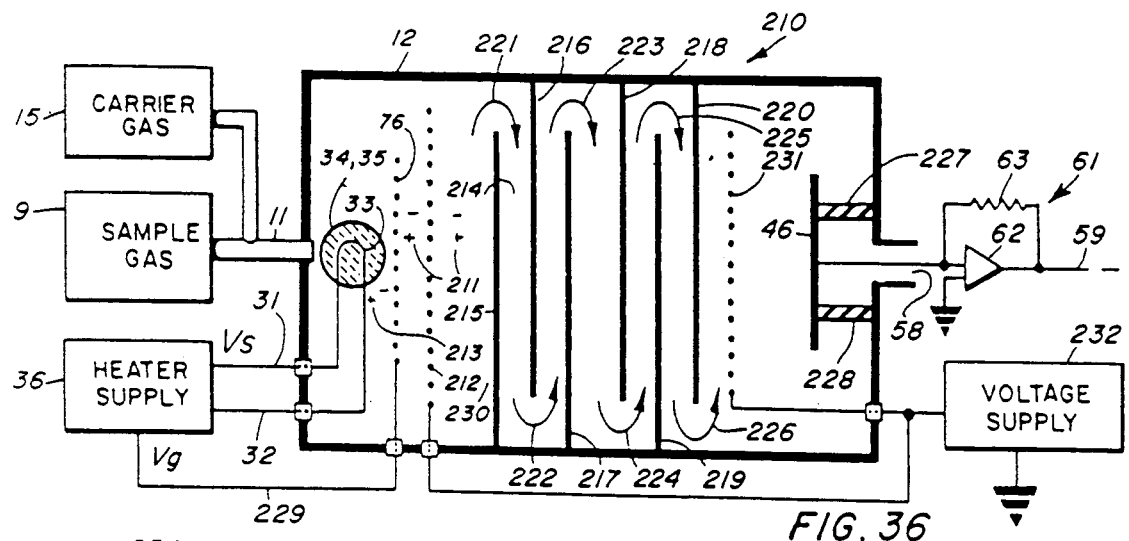
FIG. 36 is a cross-section and schematic view of an alternate embodiment of the invention.

Referring to FIG. 36, an ionization detector 210 is shown. In FIG. 36, like references are used for functions corresponding to the apparatus of FIG. 5. A sample gas 9, which may include carrier gas 15, enters housing 12 at port 11 and passes over electrolytic source 34. Sample gas 9 may contact surface 35 or react with electrolytic ions 213 in the gas phase. Grid 76 provides an increased electric field at surface 35 by way of heater supply 36 potential $V_g$ over line 229. Sample gas 9 is ionized by electrolytic source 34 at surface 35 or in the gas phase to form ions 211. Ions 211 pass through grid 212 along a channel or path 214 between baffles 215-220, shown by arrows 221-226. Baffles 215-220 function to lenghten the path of ions 211 between electrolytic source 34 and collector 46. Grid 231 which may, by a plurality of wires or a screen and voltage supply 232, provide an electric field between grid 231 and collector 46 to move ions 211 to collector 46. Collector 46 is near ground potential by way of the virtual ground input of electrometer detector 61. It is understood that negative ions 211 may also be formed by electrolytic source 34. Ions 211 are collected by collector 46 are coupled to electrometer detector 61 which provides an output on lead 59. Insulators 227 and 228 function to insulate and support collector 46 with respect to housing 12. The electrolytic source 34 may be used in combination with a radioactive source 230 which may be, for example, incorporated in grid 212. For a further description of an ionization detector, reference is made to U.S. Pat. No. 3,835,328 which issued on Sept. 10, 1974 and to U.S. Pat. No. 4,075,550 which issued on Feb. 21, 1978 which are incorporated herein by reference.

Figure 37:
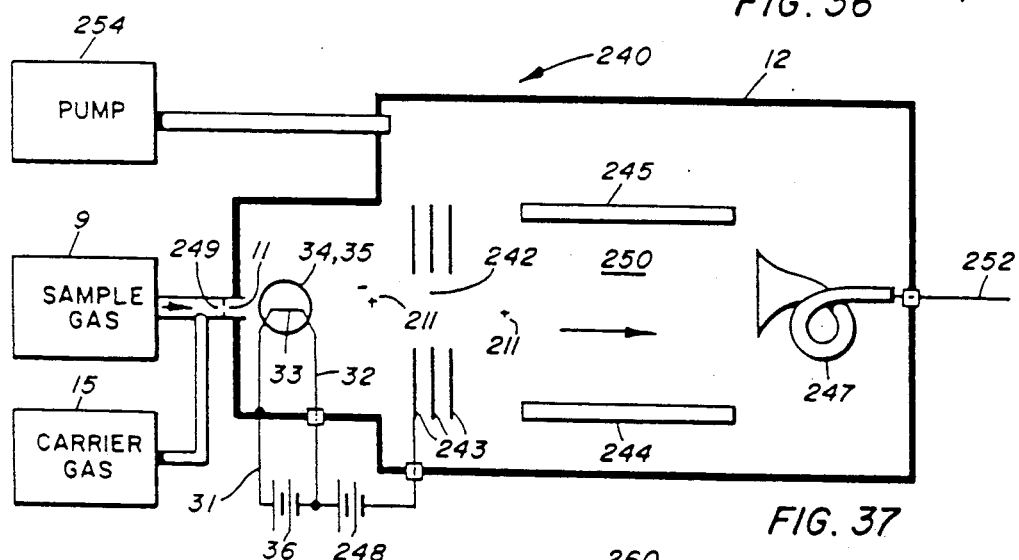
FIG. 37 is a cross-section and schematic view of an alternate embodiment of the invention.

Referring to FIG. 37, a mass spectrometer 240 is shown. In FIG. 37 like references are used for functions corresponding to the apparatus of FIGS. 1 and 36. A sample gas 9 which may include carrier gas 15 enters housing 12 at port 11 by way of, for example, pin hole 249 and passes over electrolytic source 34. Ions 211 which may be positive or negative pass through opening 242 through electrostatic lenses 243. When ions 211 enter region 250, they travel as shown by arrow 246. During their residence in region 250, the ions 211 are mass separated by means of a magnetic field (magnetic-sector mass spectrometers), cross RF and DC fields (quadrupole mass spectrometer), or other conventional means for separating ions according to charge/mass ratios. Elements 244 and 245 of FIG. 37 are two of four rods typically used in the construction of a quadrupole mass spectrometer. After ions 211 are mass analyzed, they arrive at collector 247 which may be either a Faraday plate, a channeltron (shown in FIG. 37) or an electron multiplier. An output current is coupled over lead 252. The pressure maintained within housing 12 is in the range from $10^{-5}$ Torr to $10^{-9}$ Torr by pump 254. Pin hole (e.g. 20 micron diameter) 249 can be used to couple sample gas 9 at atmospheric pressure to the reduced pressure conditions of mass spectrometer 240. Other means for introducing sample gas 9 may be a membrane inlet, by a gas chromatograph inlet, by direct deposition on source 34 which is a part of a standard solids probe, etc. Electrolyte source 34 may be used in combination with other source of ions for example electron impact, chemical ionization, field ionization, etc.

Figure 38:
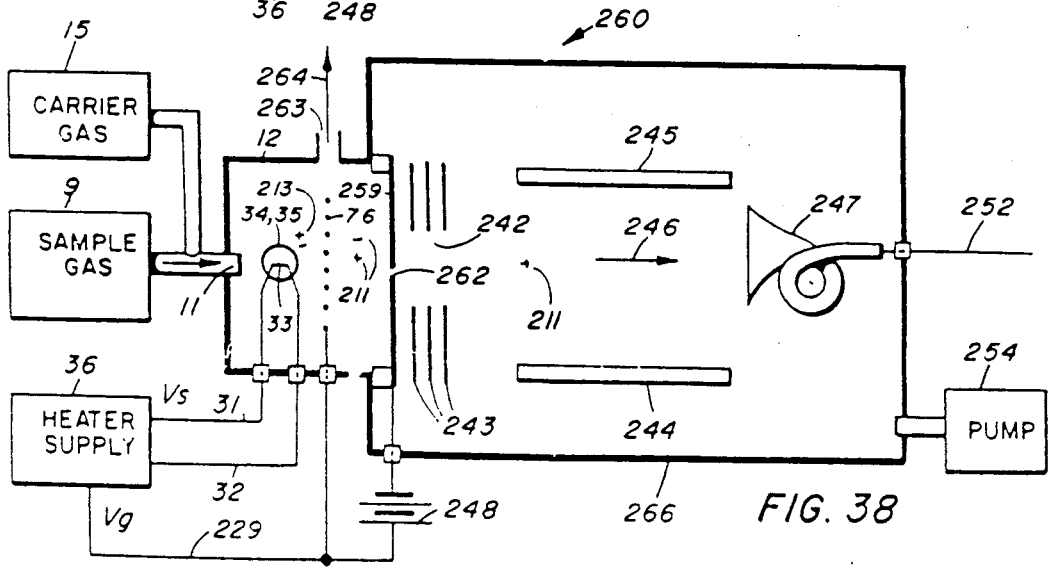
FIG. 38 is a cross-section and schematic view of an alternate embodiment of the invention.

Referring to FIG. 38 a mass spectrometer 260 is shown. In FIG. 38, like references are used for functions corresponding to the apparatus of FIG. 37. A sample gas 9 which may include carrier gas 15 enters housing 12 at port 11 at or near atmospheric pressure and passes over electrolyte source 34. Sample gas 9 may contact surface 35 or react with electrolytic ions 213 in the gas phase. Grid 76 provides an increased electric field at surface 35 by way of heater supply 36 potential $V_g$ over line 229. Sample gas 9 is ionized by electrolytic source 34 at surface 35 or in the gas phase by electrolytic ions 213 to form ions 211. Sample gas 9 exits port 263 shown by arrow 264. Ions 211 which may be positive or negative pass through inlet or pin hole 262 through electrostatic lenses 243. Voltage source 248 may apply a bias voltage to the plate 259 having pin hole 262. The ions are mass separated, for example, by a quadrupole mass spectrometer. Elements 244 and 245 are two of four rods typically used in the construction of quadrupole mass spectrometer 260. After ions 211 are mass analyzed, the separated ions arrive at collector 247 which may be either a Faraday plate, a channeltron shown in FIG. 38 or an electron multiplier. An output current is coupled over lead 252. The pressure in the region of electrostatic lens 243, elements 244 and 245 and collector 246 is maintained in the range from $10^{-5}$ to $10^{-9}$ Torr by pump 254 and housing 266. Housing 12 is coupled to housing 266 by inlet or pin hole 262.

The invention describes an ion mobility spectrometer or detector for identifying one or more constituents in a gas comprising means for introducing the gas into a reaction region, an electrolyte such as an alkali salt which may, for example, include rubidium sulfate or cesium iodide positioned in the reaction region having a surface exposed to the gas, a heating element for heating the electrolyte to a predetermined temperature to provide an ion reaction between the electrolyte and selected constituents in the gas to form ion products in the gas, electrodes for providing an electric field inside the housing across the ion products to move the ion products away from the electrolyte surface, and further electrodes for measuring the drift mobility and quantity of the ion products, whereby the presence of certain ion products may be indicated.

The invention further provides a method for generating ion products in an ion mobility spectrometer, ionization detector, and mass spectrometer from gas constituents or trace compounds in an ambient gas comprising the steps of heating an electrolyte, for example, an alkali salt to a predetermined temperature and passing the ambient gas over the electrolyte, whereby an ion reaction with the constituent gas generates the ion products. The invention provides highly sensitive, chemical class and compound specific detection of trace gases and compounds.

The invention claimed is:

1. A method for generating product ions from sample molecules in an ion mobility spectrometer, comprising the steps of:

positioning an electrolytic ionization source consisting essentially of an electrolyte in a reaction region;

heating said electrolyte to generate reactant cations;

using an electric field to assist in the extraction of the reactant cations into the gas phase;

transporting said sample molecules in a carrier gas to said reaction region to be mixed with the reactant cations, causing ion-molecule reactions between said sample molecules and reactant cations in the gas phase, said ion-molecule reactions occurring proximate to and at a distance from said electrolyte;

whereby said ion-molecule reactions produce product ions independently of said carrier gas composition and without a need for hydrogen to catalyze said ion-molecule reactions; and submitting said product ions to a drift tube of said ion mobility spectrometer for separation of said reactant cations from said product ions, and for separation of said product ions which have different mobilities.

2. The method according to claim 1, wherein said electrolyte is a solid electrolyte.

3. The method according to claim 2, wherein said solid electrolyte is coated on a heating element.

4. The method according to claim 3, wherein said heating element is a filament.

5. The method according to claim 2, wherein a heating element is embedded in said solid electrolyte.

6. The method according to claim 5, wherein said heating element is a filament.

7. The method according to claim 1, wherein said electrolyte is a salt.

8. The method according to claim 7, wherein said salt is coated on a heating element.

9. The method according to claim 8, wherein said heating element is a filament.

10. A method for generating product ions from sample molecules in an ion mobility spectrometer, comprising the steps of:

positioning an electrolytic ionization source consisting essentially of an electrolyte in a reaction region;

heating said electrolyte to generate reactant anions;

using an electric field to assist in the extraction of the reactant anions in the gas phase;

transporting said sample molecules in a carrier gas to said reaction region to be mixed with the reactant anions, thereby causing ion-molecule reactions between said sample molecules and reactant anions in the gas phase, said ion-molecule reactions occurring proximate to and at a distance from said electrolyte;

whereby said ion-molecule reactions produce product ions independently of said carrier gas composition and without a need for hydrogen to catalyze said ion-molecule reactions; and submitting said product ions to a drift tube of said ion mobility spectrometer for separation of said reactant anions from said product ions, and for separation of said product ions which have different mobilities.

11. The method according to claim 10, wherein said electrolyte is a solid electrolyte.

12. The method according to claim 11, wherein said solid electrolyte is coated on a heating element.

13. The method according to claim 12, wherein said heating element is a filament.

14. The method according to claim 11, wherein a heating element is embedded in said solid electrolyte.

15. The method according to claim 14, wherein said heating element is a filament.

16. The method according to claim 10, wherein said electrolyte is a salt.

17. The method according to claim 16, wherein said salt is coated on a heating element.

18. The method according to claim 17, wherein said heating element is a filament.

19. A method for generating product ions from sample molecules in an ion mobility spectrometer, comprising the steps of:

applying a sample consisting essentially of a salt to a filament;

inserting said filament with said sample into a reaction region of said ion mobility spectrometer;

heating said filament to cause emission of product ions, the ions being characteristic of said sample;

using an electric field to assist in the extraction of the product ions;

whereby said step of heating the filament produces said product ions independently of said carrier gas composition and without a need for hydrogen to catalyze said emission of product ions; and submitting said product ions to a drift tube of said ion mobility spectrometer for separation of said product ions which have different mobilities.

* * * * *